United States Patent
Zaid et al.

(10) Patent No.: US 11,578,070 B2
(45) Date of Patent: Feb. 14, 2023

(54) HARMINE SYNTHESIS

(71) Applicant: Ankh Life Sciences Limited, Dublin (IE)

(72) Inventors: Gene H. Zaid, Hutchinson, KS (US); Krishna Mohan Donavalli, Wichita, KS (US); Rajni Verma, Wichita, KS (US)

(73) Assignee: Ankh Life Sciences Limited, Dublin (IE)

( * ) Notice: Subject to any disclaimer, the term of this patent is extended or adjusted under 35 U.S.C. 154(b) by 242 days.

(21) Appl. No.: 17/009,115

(22) Filed: Sep. 1, 2020

(65) Prior Publication Data

US 2022/0064156 A1     Mar. 3, 2022

(51) Int. Cl.
*C07D 471/04* (2006.01)
*B01J 31/02* (2006.01)

(52) U.S. Cl.
CPC ........ *C07D 471/04* (2013.01); *B01J 31/0209* (2013.01)

(58) Field of Classification Search
CPC .................................................. C07D 471/04
See application file for complete search history.

(56) References Cited

PUBLICATIONS

Begum et al., "Preparation, tructure and spasmolytic activities of some dervatives of harmine series of alkaloids." Natural Product Research: Formerly Natural Product Letters, 20:3, 213-227; published online 2007.
Brobst et al., "The Free Base Extraction of Harmaline from Penganum harmala." American Journal of Undergraduate Research 8 2-3 (2009): 1-4.
Wang et al., "Separation and purification of harmine and harmaline from Peganum haramala using pH-zone-refining counter-current chromatography." J Sep.Sci. 2008, 31, 3543-3547.

*Primary Examiner* — Paul V Ward
(74) *Attorney, Agent, or Firm* — Hovey Williams LLP

(57) ABSTRACT

Methods for the synthesis of harmine comprise reacting harmaline with 2,3-dichloro-5,6-dicyano-1,4-benzoquinone (DDQ) in the presence of a diacid catalyst. In an embodiment, the synthesis is carried out using a reaction mixture of harmaline, DDQ, THF solvent, and succinic acid; the reaction is carried out under an inert atmosphere with refluxing for a period of 4-12 hours.

11 Claims, No Drawings

HARMINE SYNTHESIS

BACKGROUND OF THE INVENTION

Field of the Invention

The present invention is broadly concerned with diacid-catalyzed syntheses of harmaline to harmine in the presence of 2,3-dichloro-5,6-dicyano-1,4-benzoquinone (DDQ). The syntheses give substantially quantitative production of harmine.

Description of the Prior Art

Harmaline and harmine are harmala alkaloids which have been used for centuries for medicinal and other purposes. In past practices, these compounds have been extracted from *Peganum harmala* (also known as Syrian Rue) using a variety of different solvents. While harmaline is the most plentiful alkaloid from this plant, both alkaloids are present only in relatively small amounts. Therefore, simple solvent extraction of these alkaloids is not commercially viable when kilogram quantities thereof are needed. Bulk harmaline is cheaper to purchase than harmine, and therefore if harmaline could be economically converted to harmine, such would be a significant advance.

Prior extractive techniques for obtaining harmala alkaloids are described in the following references: Begum, Sabira et al., "Preparation, structure and spasmolytic activities of some derivatives of harmine series of alkaloids," Natural Product Research, Vol. 20, No. 3, 2006, pp. 213-217; Brobst, Alyssa et al., "The Free Base Extraction of Harmaline from *Penganum harmala,*" American Journal of Undergraduate Research, Vol., 8, Nos. 2&3, 2009; and Wang, Xiao et al., "Separation and purification of harmine and harmaline from *Peganum harmala* using pH-zone-refining counter-current chromatography," J. Sep. Sci. 31, 2008, pp. 3543-3547.

SUMMARY OF THE INVENTION

Non-extracted syntheses of harmaline and harmine have been developed by the assignee of this patent application. The developed synthesis of harmaline is a complicated undertaking, but still is economically superior to solvent extractions. In another synthesis effort, synthetic harmaline has been converted to harmine by the use of a Pd catalyst. However, this catalyst is extremely expensive, with the result that the cost of harmaline may approach or even exceed $200,000 per kilogram.

The present invention overcomes these issues, providing a method of synthesizing harmine comprising the steps of reacting a reaction mixture comprising harmaline with DDQ in a compatible solvent and in the presence of an acid catalyst, and thereafter recovering harmine. The acid catalyst is preferably a diacid, and particularly saturated C2-C10 diacid, where the carbon chain may be linear, branched, or cyclic. Linear diacids, and especially the C3-C6 linear diacids, provide substantially quantitative conversions of harmaline to harmine.

In the reaction mixture, the DDQ may be present in a molar excess as compared with harmaline, and the solvent may be any suitable non-interfering solvent. Such solvents may be selected from the group consisting of THF, dichloromethane, ethyl acetate, toluene, ethers such as dibutyl ether or cyclopentyl methyl ether, dimethoxyethane, acetonitrile, dichloroethane, and mixtures thereof.

The reaction is preferably carried out under an inert atmosphere, usually $N_2$, with refluxing for a period of from about 4-12 hours. Purification of the final product can be accomplished by a variety of means, such as chromatography.

DETAILED DESCRIPTION OF THE PREFERRED EMBODIMENT

Generally speaking, the invention pertains to a synthesis of harmine involving acid-catalyzed dehydrogenation of harmaline by DDQ to give substantially quantitative yields of harmine. The overall reaction is:

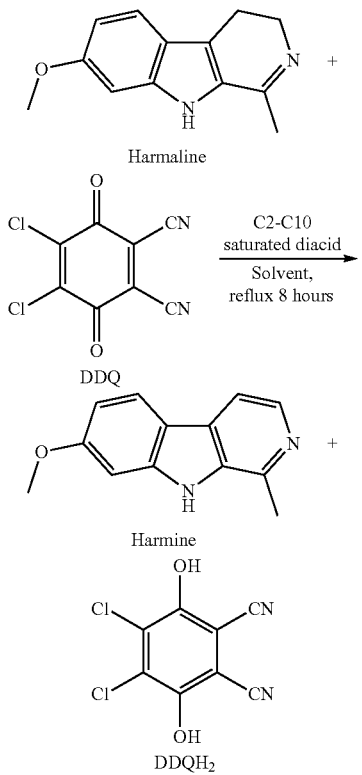

In the synthesis, the DDQ is typically present in a molar excess as compared with the harmaline. The acid catalyst is preferably a C2-C10 saturated diacid, where the carbon chain may be linear, branched, or cyclic. The most readily available diacids are the linear dicarboxylic acids, such as:

| Common name | Systematic IUPAC name | Structure |
|---|---|---|
| Oxalic acid | ethanedioic acid | HOOC–COOH |
| Malonic acid | propanedioic acid | HOOC–CH$_2$–COOH |
| Succinic acid | butanedioic acid | HOOC–(CH$_2$)$_2$–COOH |
| Glutaric acid | pentanedioic acid | HOOC–(CH$_2$)$_3$–COOH |
| Adipic acid | hexanedioic acid | HOOC–(CH$_2$)$_4$–COOH |
| Pimelic acid | heptanedioic acid | HOOC–(CH$_2$)$_5$–COOH |
| Suberic acid | octanedioic acid | HOOC–(CH$_2$)$_6$–COOH |
| Azelaic acid | nonanedioic acid | HOOC–(CH$_2$)$_7$–COOH |
| Sebacic acid | decanedioic acid | HOOC–(CH$_2$)$_8$–COOH |

The solvent can be selected from any non-interfering solvent which will support the reaction. A typical example is tetrahydrofuran (THF), although other possibilities exist.

The reaction is preferably carried out in an inert atmosphere, typically nitrogen gas, for a period of from about 4-12 hours, with refluxing. The crude reaction mixture is then treated to recover the harmine product using solvent extraction and chromatography.

EXAMPLES

Example 1

In this example, harmaline (previously dried using a Dean-Stark apparatus under N$_2$) and DDQ were reacted in the presence of succinic acid and dried THF solvent (THF dried by boiling with sodium metal and benzoquinone under N$_2$).

Specifically, harmaline was added to a round-bottom flask, followed by 1.5 equivalents of DDQ and an excess of succinic acid, in a glove bag under nitrogen. After initial mixing, the flask was connected with a condenser and moved to a hood. The THF was then added to the flask and the mixture was refluxed for 8 hours under N$_2$.

After refluxing, the reaction mixture was cooled to room temperature and 1M sodium hydroxide was added with stirring for 5 minutes. The pH of the aqua layer was measured to confirm that the pH was basic, and the organic layer was separated from the aqua layer with 5 equivalents of acetone. This separated solution was then concentrated using a rotary evaporator to provide a crude solid. This solid was dissolved in dichloromethane, followed by vacuum filtration on a celite pad/cake to remove solid impurities. The organic solution was then dried over anhydrous ammonium sulfate (Na2SO4) and concentrated using the rotary evaporator to obtain a dark brown solid. Purification was performed using column chromatography with a solvent system of 10% methanol in dichloromethane. The purified product was analyzed using NMR for the presence of harmaline and harmine. No harmaline characteristic peaks were observed in the final product, confirming the essentially quantitative production of harmine.

The same procedure was carried out except that no succinic acid or other diacid catalyst was used. This resulted in a final product containing substantial amounts of harmaline. Thus, performing the reaction in the absence of acid catalyst resulted in incomplete conversion to harmine.

While not wishing to be bound by any theory, it is believed that the conversion synthesis of harmine using harmaline as a starting reactant involves a stepwise reaction according to the following reaction scheme:

Step 1: Conversion of DDQ to DDQH

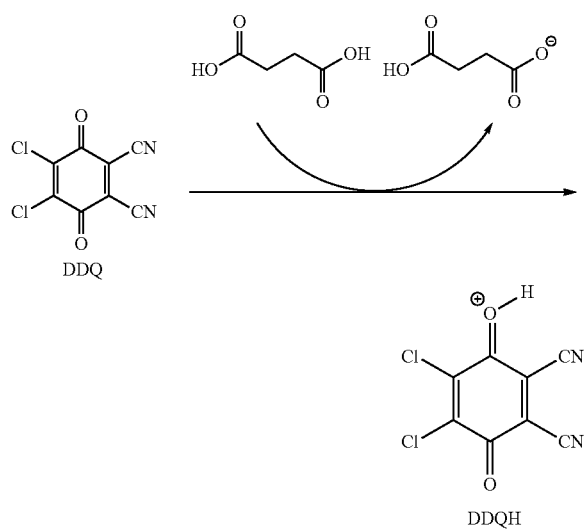

Step 2: Dehydrogenation of Harmaline by DDQH and 3-carboxypropanoate

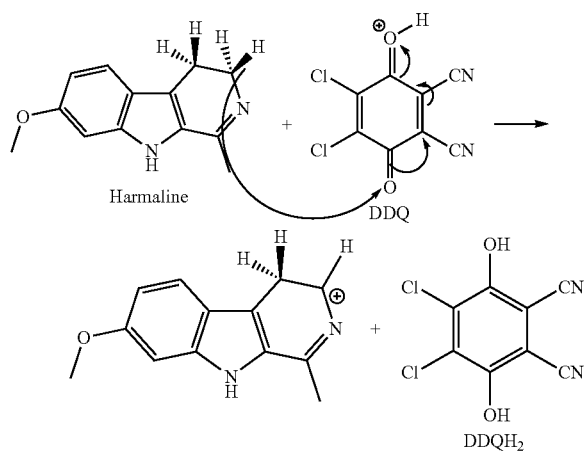

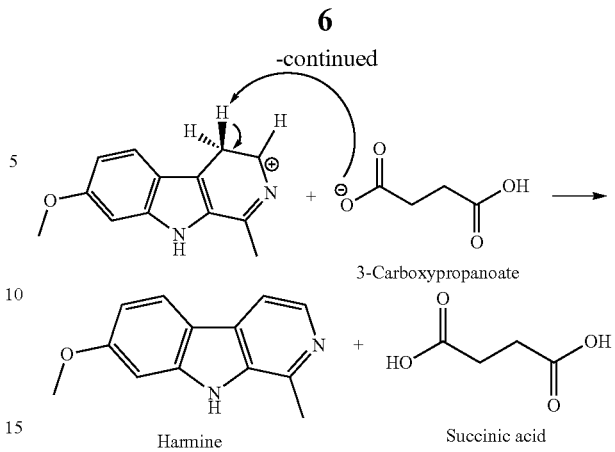

Example 2

The above Example 1 synthesis of harmine was repeated three times except that oxalic, maleic, and glutaric acids were used in lieu of succinic acid. All three syntheses were successful and yielded high levels of conversion of harmaline to harmine. However, succinic is generally less expensive than these other diacids, and is therefore preferred.

We claim:

1. A method of synthesizing harmine comprising the steps of reacting a reaction mixture comprising harmaline with 2,3-dichloro-5,6-dicyano-1,4-benzoquinone (DDQ) in a compatible solvent and in the presence of an acid catalyst, and thereafter recovering harmine.

2. The method of claim 1, said acid catalyst being a diacid.

3. The method of claim 2, said diacid being selected from the group consisting of saturated C2-C10 diacids, where the carbon chain may be linear, branched, or cyclic.

4. The method of claim 3, said diacid selected from the group consisting of C2-C10 linear diacids.

5. The method of claim 4, said diacid selected from the group consisting of C3-C6 linear diacids.

6. The method of claim 1, where said DDQ is present in a molar excess as compared with harmaline.

7. The method of claim 1, said reaction carried out under an inert atmosphere.

8. The method of claim 1, including the step of refluxing said reaction mixture for a period of from about 4-12 hours.

9. The method of claim 1, said recovery step comprising the step of purifying the reaction product of the reaction using chromatography.

10. The method of claim 1, said solvent selected from the group consisting of THF, dichloromethane, ethyl acetate, toluene, ethers such as dibutyl ether or cyclopentyl methyl ether, dimethoxyethane, acetonitrile, dichloroethane, and mixtures thereof.

11. The method of claim 10, wherein said solvent is THF.

* * * * *